United States Patent [19]

Urry et al.

[11] 4,132,746

[45] Jan. 2, 1979

[54] SYNTHETIC ELASTOMERIC INSOLUBLE CROSS-LINKED POLYPENTAPEPTIDE

[75] Inventors: Dan W. Urry, Vestavia Hills; Kouji Okamoto, Birmingham, both of Ala.

[73] Assignee: University of Alabama, Birmingham Medical & Education Foundation, Birmingham, Ala.

[21] Appl. No.: 704,088

[22] Filed: Jul. 9, 1976

[51] Int. Cl.$^2$ .............................................. C08G 69/10
[52] U.S. Cl. ................................ 260/857 TW; 3/1.4; 3/1.9; 128/92 G
[58] Field of Search .......................... 128/92 C, 92 G; 260/78 A, 857 TW

[56] References Cited

U.S. PATENT DOCUMENTS

| 3,867,352 | 2/1975 | Akamatsu et al. | 260/78 A |
| 3,948,863 | 4/1976 | Akamatsu et al. | 260/78 A |

*Primary Examiner*—Harold D. Anderson
*Attorney, Agent, or Firm*—Bacon & Thomas

[57] ABSTRACT

An insoluble cross-linked polypentapeptide is totally synthesized by preparing two modified linear polypentapeptides patterned on the polypentapeptide from the pentapeptide ($Val_1$-$Pro_2$-$Gly_3$-$Val_4$-$Gly_5$) one of the repeating peptide sequences contained in tropoelastin, the precursor protein of the core of the elastic fiber of the vascular wall, and by cross-linking the modified polypentapeptides. One of the intermediate polypentapeptides is modified by replacing a portion of at least one of the amino acid residues with the residue of an amino acid having more than one amino function and the other is modified by replacing a portion of at least one of the amino acid residues with the residue of an amino acid having more than one carboxyl function, to provide free amino groups on the one intermediate and free carboxyl groups on the other for interreaction in the presence of a suitable cross-linking agent.

The resulting cross-linked insoluble polypentapeptide is elastomeric in nature and capable of calcification by withdrawing calcium ions from a serum medium, thus making it useful as a calcifiable matrix for the formation of an artificial bone structure. The calcifiable material can be treated to make it useful in artificial vascular wall formation.

18 Claims, 10 Drawing Figures

SYNTHETIC ELASTOMERIC INSOLUBLE CROSS-LINKED POLYPENTAPEPTIDE

BACKGROUND OF THE INVENTION

The fibrous elastic fiber, a primary site of lipid deposition and calcification in the vascular wall, derives from intermolecular cross-linking of lysyl residue side chains.[1,2] The precursor protein of the core of the elastic fiber, tropoelastin,[3-6] has been shown to contain repeating peptide sequences[7,8] — a tetrapeptide ($Val_1$-$Pro_2$-$Gly_3$-$Gly_4$), a pentapeptide ($Val_1$-$Pro_2$-$Gly_3$-$Val_4$-$Gly_5$), and a hexapeptide ($Ala_1$-$Pro_2$-$Gly_3$-$Val_4$-$Gly_5$-$Val_6$) it being understood that Val represents the residue of valine, Pro the residue of proline, Gly the residue of glycine, Ala the residue of alanine and the subscripts the position in the peptide molecule, all of the amino acid residues, with the exception of that of glycine, being in the L-configuration. These sequences, their oligomers and high polymers have been synthesized and their conformations characterized.[9-14]

The molecular system of interest has been examined in three different states — solution, coacervate and fibrous. The coacervate is the key to bridging from the solution to the fibrous state. Coacervation, a reversible, concentration-dependent phase separation elicited in this case by temperature, is an uncommon property exhibited by tropoelastin, by α-elastin (a chemical fragmentation product of fibrous elastin), by the polypentapeptide and by the polyhexapeptide. All of these molecular systems are soluble in water at low temperatures, but, on raising the temperature, the solutions become cloudy and the light scattering elements coalesce to form a more dense phase which is about 60% water by volume. The coacervate is the stable state at body temperature; the coacervate contains the same volume percent water (~60%) as fibrous elastin, and the coacervate is filamentous with periodicities similar to those of fibrous elastin. For these reasons, the coacervate is taken to be a model of the relaxed fibrous state and the process of coacervation is viewed as a key step in elastogenesis which concentrates and aligns the subunit prior to covalent crosslinking.

All of the prior research, however, has failed to result in the obtaining of a product sufficiently insoluble to have practical utility in physiological applications.

REFERENCES:
1. Partridge, S. M. (1969) Gerontologia 15, 85–100.
2. Franzblau, C. and Lent, R. W. (1969) in Structure, Function and Evolution in Proteins, Brookhaven Sympos. Biol. 21, 358–377.
3. Smith, D. W. Weissman, N. and Carnes, W. H. (1968) Biochem. Biophys. Res. Commun. 31, 309–315.
4. Sandberg, L. B., Weissman, N. and Smith, D. W. (1969) Biochemistry 8, 2940–2945.
5. Smith, D. W., Abraham, P. A. and Carnes, W. H. (1975) Biochem. Biophys. Res. Commun. 66, 893–899.
6. Narayanan, A. A., Page, R. C. (1976) J. Biol. Chem. 251(4) 1125–1130.
7. Gray, W. R., Sandberg, L. B. and Foster, J. A. (1973) Nature 246, 461–466.
8. Foster, J. A., Bruenger, E., Gray, W. R. and Sandberg, L. B. (1973) J. Biol. Chem. 248, 2876–2879.
9. Urry, D. W., Cunningham, W. D. and Ohnishi, T. (1974) Biochemistry 13, 609–615.
10. Urry, D. W. and Ohnishi, T. (1974) Biopolymers 13, 1223–1242.
11. Urry, D. W. and Ohnishi, T. (1974) in Peptides, Polypeptides and Proteins, ed. by F. A. Bovey, M. Goodman and N. Lotan, John Wiley and Sons, Inc., pp. 230–247.
12. Urry, D. W., Mitchell, L. W. and Ohnishi, T. (1975) Biochem. Biophys. Acta 393, 296–306.
13. Urry, D. W. Ohnishi, T., Long, M. M. and Mitchell, L. W. (1975) Int. J. Pept. Protein Res. 7, 367–378.
14. Urry, D. W., Mitchell, L. W. Ohnishi, T. and Long, M. M. (1975) J. MOl. Biol. 96, 101–117.

DETAILED DESCRIPTION OF THE INVENTION

The invention will be described in detail with reference to the accompanying drawings in which:

FIGS. 1A, 1B and 1C together constitute is a depiction of the proton magnetic resonance spectra of the three pentameric units which are incorporated into a preferred cross-linked high polymer of the invention;

FIGS. 2A, 2B and 2C together constitute is a depiction of the proton magnetic resonance spectra of two high polymer intermediates which are cross-linked to form a preferred cross-linked high polymer of the invention and for comparison the proton magnetic resonance spectrum of a similar high polymer without the cross-linking residues;

Figure 1A:
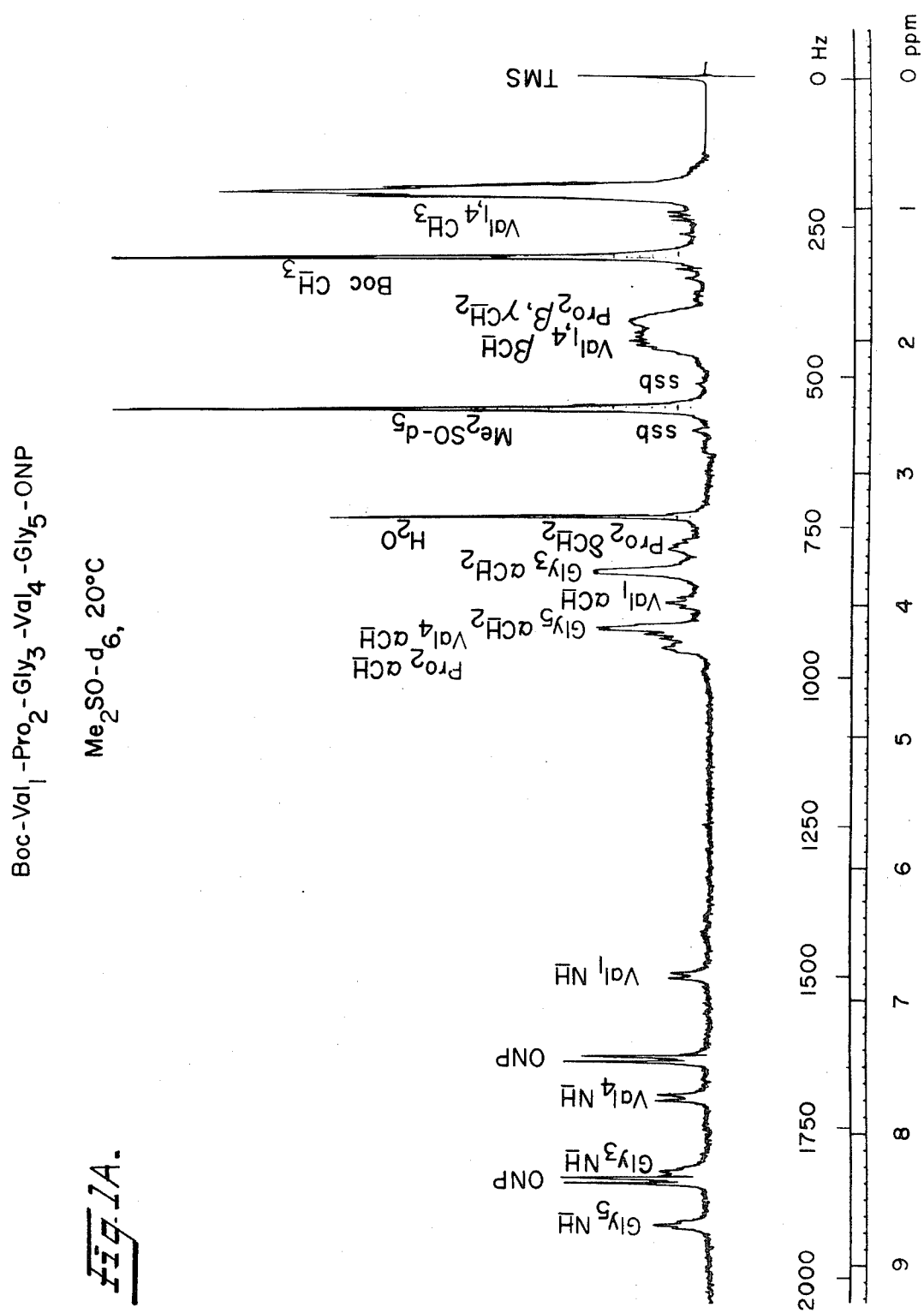

The synthetic elastomeric water-soluble cross-linked polypentapeptide of the invention is prepared by cross-linking intermediate linear high polymers patterned on the polypentapeptide from the pentapeptide ($Val_1$-$Pro_2$-$Gly_3$-$Val_4$-$Gly_5$) one of the repeating peptide sequences contained in tropoelastin, the precursor protein of the core of the elastic fiber of the vascular wall. One of the intermediates, which are themselves novel and constitute a feature of the invention, has a portion of at least one of the amino acid residues replaced by the residue of an amino acid having more than one amino function. Another of the intermediates has a portion of at least one of the amino acid residues replaced by the residue of an amino acid having more than one carboxyl function.

The invention will now be described with respect to a preferred type of cross-linked polypentapeptide in which the amino acid residue furnishing free amino cross-linking sites is derived from lysine and the amino acid residue furnishing free carboxyl cross-linking sites is derived from glutamic acid. In this product, because of conformational considerations, it is the valine residue in position-4 of the pentameric unit ($Val_1$-$Pro_2$-$Gly_3$-$Val_4$-$Gly_5$) which is replaced in each instance.

It is to be understood, however, that residues of other amino acids having more than one amino function and more than one carboxyl function can be introduced into the intermediates and that this can be done at any position in each of the intermediates by methods similar to that now to be described.

The preferred type of cross-linked polypentapeptide according to the invention may be totally synthesized using the following reaction scheme:

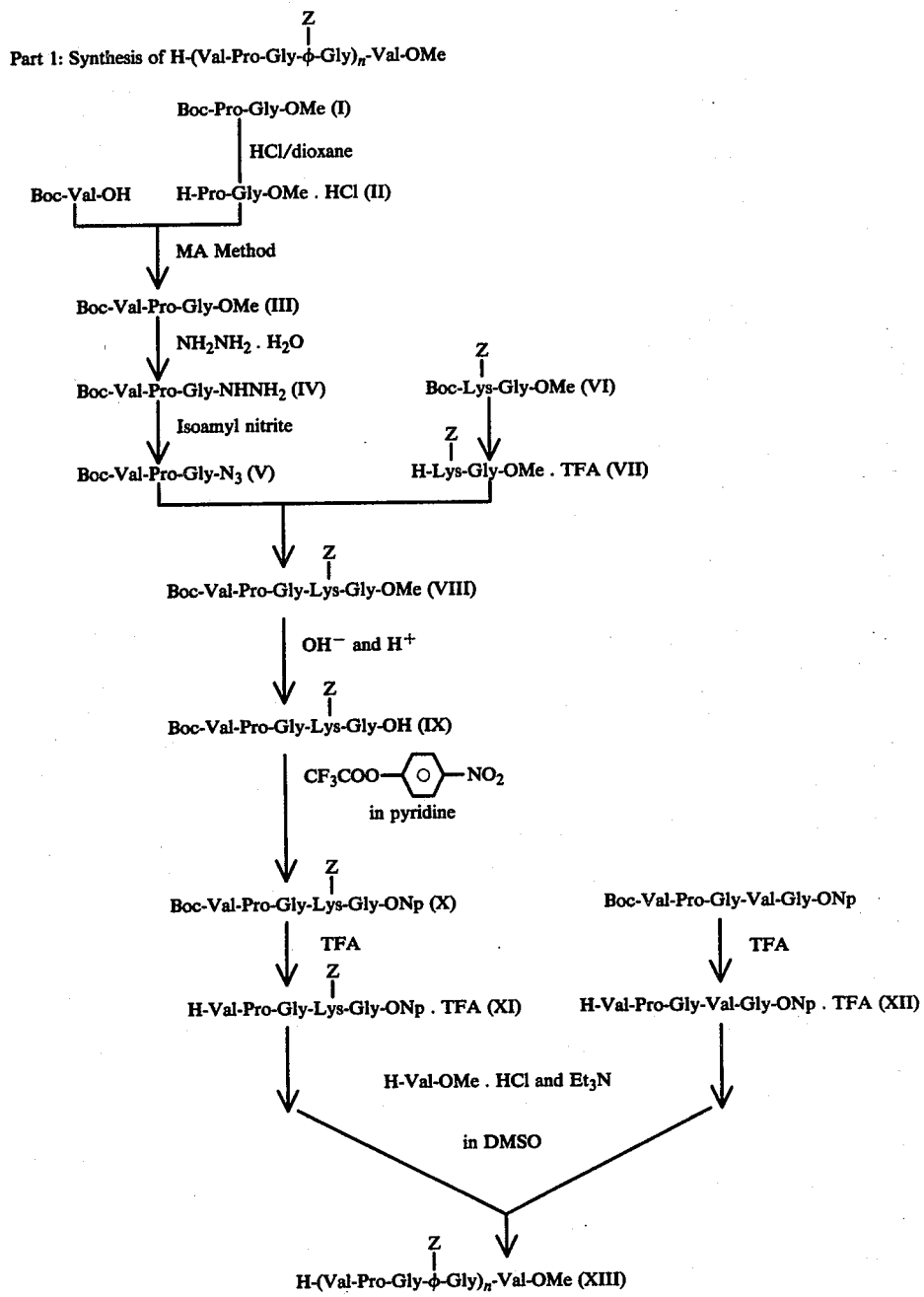

Part 1: Synthesis of H-(Val-Pro-Gly-φ-Gly)$_n$-Val-OMe

Part 2: Synthesis of H-(Val-Pro-Gly-φ'-Gly)$_n$-Val-OMe

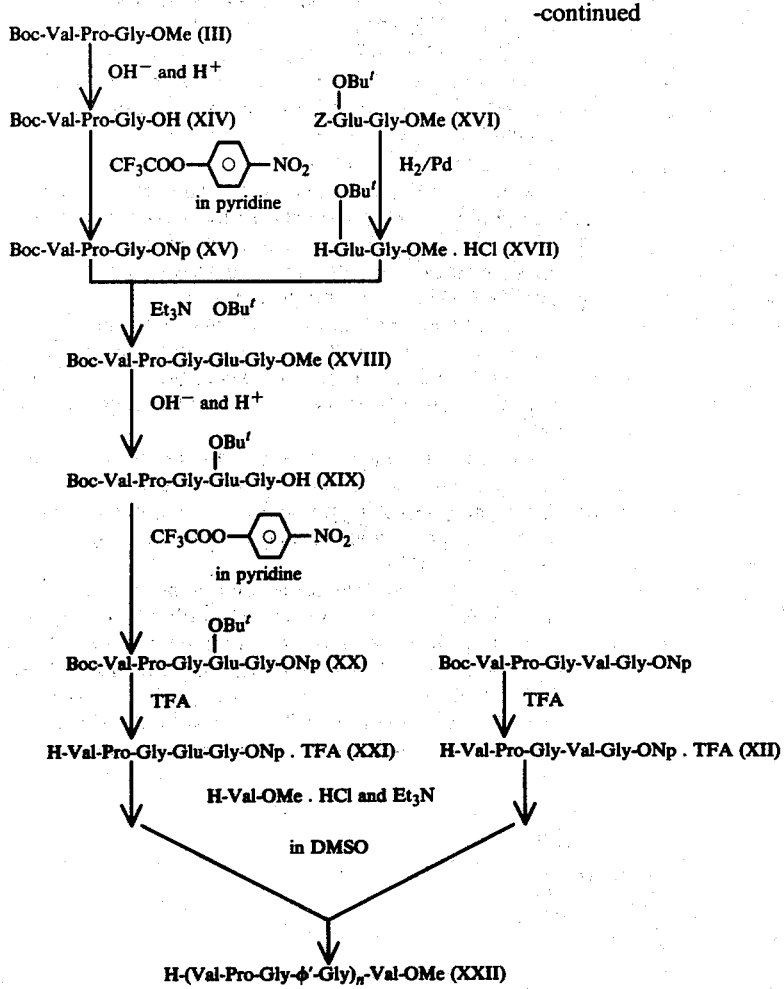

Part 3: Synthesis of Cross-Linked H-(Val-Pro-Gly-ψ-Gly)$_n$-Val-OMe
          Z

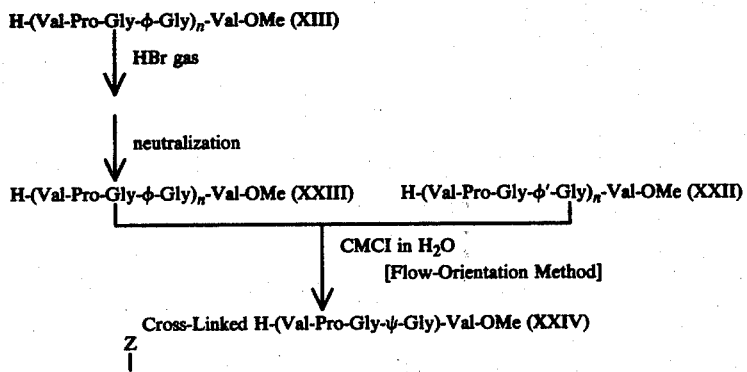

φ = Val or Lys wherein Z = benzyloxycarbonyl
    (both of the pentapeptide units being present)

φ' = Val or Glu (both of the pentapeptide units being present)
ψ = Val, Lys or Glu (all three of the pentapeptide units being present)
Boc = t-butyloxycarbonyl  Np = p-nitrophenyl
TFA = trifluoroacetic acid
DMSO = dimethylsulfoxide
CMCI = 1-cyclohexyl-3-(2-morpholinoethyl)-carbodiimide metho-p-toluenesulfonate [also designated 1-cyclohexyl-3-(2-N-methylmorpholinoethyl)-carbodiimide-p-toluenesulfonate]
Bu$^t$ = t-butyl
n = the average number of pentapeptide units in each chain length
All amino acid residues are in the L-configuration with the exception of that of glycine.

It will be understood that other groups known for blocking amino groups and carboxyl groups can be used in place of those specified in the above reaction scheme.

The proportions of the residue of an amino acid having more than one amino function; introduced into one of the intermediate linear high polymers and of the residue of an amino acid having more than one carboxyl function introduced into the other of the intermediate linear high polymers are not critical. In general, the Val$_4$:Lys ratio can vary from 1:1 to 10:1, with a ratio of 3:1 being preferred, and the Val$_4$:Glu ratio can vary from 1:1 to 10:1, with a ratio of 3:1 being preferred. The ratio of intermediate XXII to intermediate XXIII can vary from 4:1 to 1:4, with a 1:1 ratio being preferred where the Val$_4$:Lys and Val$_4$:Glu ratios are the same.

The two linear polymers will each contain from 10 to 100 pentapeptide units, with about forty such units being preferred.

The cross-linking agent is specified in the reaction scheme as 1-cyclohexyl-3-(2-morpholinoethyl)-carbodiimide metho-p-toluenesulfonate, but while this cross-linking agent is preferred, it is to be understood that other cross-linking agents, for example, EDCI [1-ethyl-3-(3-dimethylaminopropyl) carbodiimide.HCl] and Nepis or Woodward's Reagent K (N-ethyl-5-phenylisoxazolium-3'sulfonate), can be employed. When the preferred cross-linking agent is used, it is believed to effect cross-linking in accordance with the following mechanism:

The cross-linked insoluble elastomeric polypentapeptide of the invention has been found to withdraw calcium ions from blood serum so as to be calcified throughout, and this will occur even through a semipermeable membrane. This causes the product to be suitable as a matrix for replacing or repairing bone structure in the animal body.

Because of this property, it is apparent that the synthetic cross-linked polypentapeptide would not be suitable for use as an artificial vascular wall material, but it has been found that it can be inactivated to make it highly suitable for this purpose. For example, the cross-linked polypentapeptide can be formed into the size and shape of a blood vessel to be replaced by carrying out the cross-linking reaction between the walls of two concentric cylinders, one of which is being continually rotated.

The resulting shaped material can then be inactivated by treatment with a glycoprotein or a proteoglycan. For example, calcification of elastin polypentapeptides can be prevented by addition of commercially available chondroitin sulfate.

The amino acid derivatives used in the specific example to follow, which is presented as illustrating but not as limiting the invention, were commercially available and could be used without further purification: Boc-Pro-OH, Boc-Val-OH, and Z-Glu ($\gamma$-OBu$^t$)-OH from Bachem, Inc.; Boc-Lys ($\epsilon$-Z)-OH and H-Val-OMe.HCl from Protein Research Foundation, Japan; H-Gly-

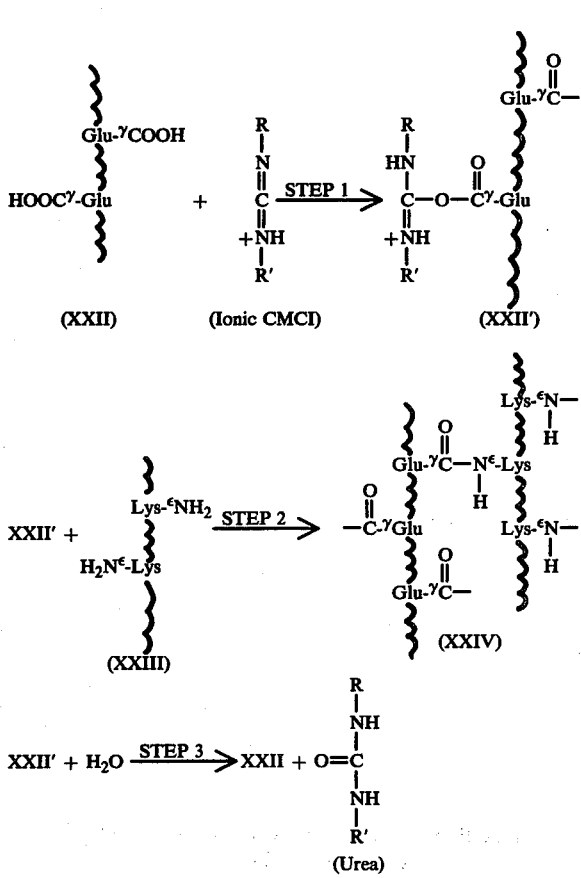

The cross-linking reaction can be carried out under static conditions but it is preferred that there be employed a flow orientation technique which will be described in the specific example of practice to follow.

OMe.HCl from Sigma Chemical Company.

Melting points were determined with a Thomas Hoover apparatus and were uncorrected. The elemental analyses were carried out by a commercial testing laboratory.

For amino acid analyses samples (1-2 mg) of the synthetic intermediates and cross-linked polypentapeptide were hydrolyzed with 6N hydrochloric acid (2 ml) for 48-60 h in an evacuated, sealed tube at 110°. The hydrolyzates were analyzed on a Beckman 119 H amino acid analyzer using the ninhydrin method.

Thin-layer chromatography (TLC) was performed on silica gel G (Quantum Industries) with the following solvent systems: $Rf^1$, chloroform:methanol:acetic acid (95:5:3, $v/v$); $Rf^2$, chloroform:methanol (5:1, $v/v$); $Rf^3$, n-butanol:acetic acid: pyridine:water (15:3:10:12, $v/v$). Detection of TLC plates was done by spraying ninhydrin for a material with a free amino group, by spraying 48% HBr and ninhydrin for molecules with a Z or Boc group, by chlorine/tolidine reaction for those with peptide bonds.

The proton magnetic resonance (pmr) spectra of the synthetic intermediates prior to polymerizing were obtained on a Varian HR 220 MHz spectrometer equipped with a tracking frequency decoupling accessory and with an SS-100 computer of 16K for multiscan averaging. Sample temperature was calibrated with methanol or ethylene glycol chemical shifts and controlled to within ±2°. The carbon-13 magnetic resonance (cmr) spectra of the synthetic polypentapeptides prior to cross-linking were obtained on a JEOL PFT-100 pulse spectrometer operating at 25.15 MHz with a deuterium lock and with proton noise decoupling. An EC-100 computer system containing 20K of a Texas Instruments 980 A computer was used for accumulation of the free induction decay of each pulse. Pulse width was 15 $\mu$sec and the repetition rate was 1 sec. The temperature was maintained by a JES VR-3 variable temperature unit. In both spectrometers, tetramethyl silane was used as an internal reference in the organic solvents.

EXAMPLE (a) Boc-Pro-Gly-OMe (I)

To a solution of Boc-Pro-OH (73.2 g, 340 mmol) and triethylamine (47.6 ml, 340 mmol) in tetrahydrofurane (300 ml), cooled to −10°, was added isobutyl chloroformate (44.5 ml, 340 mmol). After 15 min., a solution of H-Gly-OMe.HCl (42.7 g, 340 mmol) and triethylamine (47.6 ml, 340 mmol) in chloroform (300 ml) was added to the stirring solution. The mixture was stirred at 0° for 1 h and at room temperature for 24 h. The organic solvent was removed under reduced pressure and the residue, dissolved in ethyl acetate, was washed with 10% citric acid solution, 4% sodium bicarbonate solution, water and dried over anhydrous sodium sulfate. The solution was evaporated and the oily residue was crystallized on addition of petroleum ether; yield 71.8 g (84%), m.p. 70-72° C., $Rf^1$ 0.70. Calcd. for $C_{13}H_{22}N_2O_5$:C, 54.53; H, 7.75; N, 9.78%. Found: C, 55.03; H, 7.58; N, 9.34%.

(b) H-Pro-Gly-OMe.HCl (II)

A solution of I (70.0 g, 244 mmol) in 244 ml of 5.2 N hydrogen chloride in dioxane was allowed to stand for 1 h at room temperature. The reaction mixture was evaporated to dryness and the residual oil was washed with petroleum ether by decantation. This oil gave a single spot on TLC; yield 54.3 g (100%), $Rf^1$ 0.24.

(c) Boc-Val-Pro-Gly-OMe (III)

Boc-Val-OH (52.1 g, 240 mmol) was reacted with II (53.4 g, 240 mmol) by the mixed anhydride method as described for the preparation of I in part (a). The resulting oil showed a single spot on TLC; yield 64.0 g (69%), $Rf^1$ 0.69.

(d) Boc-Val-Pro-Gly-NHNH$_2$ (IV)

To a solution of III (64.0 g, 166 mmol) in methanol (50 ml) was added 95% hydrazine (120 ml, 2.49 mol) and the mixture was stirred for 1 day at room temperature. The reaction mixture was evaporated and the residue, dissolved in chloroform, was washed with water and dried over sodium sulfate. The solution was evaporated and the residue was triturated with petroleum ether. A non-crystalline product obtained gave a single spot on TLC; yield 45.8 g (72%), $Rf^1$ 0.69.

(e) Boc-Lys($\epsilon$-Z)-Gly-OMe (VI)

Boc-Lys($\epsilon$-Z)-OH (9.1 g, 24 mmol) and H-Gly-OMe.HCl (3.01 g, 24 mmol) were reacted by the mixed anhydride method as described for the preparation of I in part (a). The resulting solid was recrystallized from ethyl acetate-ether; yield 9.18 g (85%), m.p. 81.5-83° C., $Rf^1$ 0.64. Calcd. for $C_{22}H_{34}N_3O_7$: C, 58.38; H, 7.59; N, 9.29%. Found: C, 58.64; H, 7.29; N, 9.05%.

(f) H-Lys($\epsilon$-Z)-Gly-OMe.TFA (VII)

A solution of VI (9.0 g, 19.9 mmol) in 99% trifluoroacetic acid (20 ml) was allowed to stand for 15 min at room temperature. The reaction mixture was evaporated to dryness and the residual oil was washed with ether and petroleum ether by decantation. This oil gave a single spot on TLC; yield 9.56 g (103%), $Rf^1$ 0.11.

(g) Boc-Val-Pro-Gly-Lys($\epsilon$-Z)-Gly-OMe (VIII)

To a solution of IV (6.5 g, 16.9 mmol) in dimethyl formamide (30 ml) containing 9.75 ml of 5.2 N hydrogen chloride in dioxane was added isoamyl nitrite (2.49 ml-18.6 mmol). The mixture, after stirring at −20° for 15 min, was cooled to −60° and triethylamine (7.1 ml, 50.7 mmol) was added. This resulted in a solution of azide (V) to which were added VII (9.56 g, 20.5 mmol) and triethylamine (5.74 ml, 41 mmol) in dimethyl formamide (30 ml). After stirring at 0° for 3 days, the reaction mixture was evaporated and the residue, dissolved in ethyl acetate, was washed with water, 10% citric acid solution, 4% sodium bicarbonate solution, water and dried over sodium sulfate. The solution was evaporated to dryness and the resulting solid was recrystallized from ethyl acetate-ether; yield 8.5 g (71%), m.p. 140-142° C., $Rf^1$ 0.51. Calcd. for $C_{34}H_{53}N_6O_{10}$: C, 57.86; H, 7.57; N, 11.91%. Found: C, 57.92; H, 7.38; N, 11.51%.

(h) Boc-Val-Pro-Gly-Lys($\epsilon$-Z)-Gly-OH (IX)

To a solution of VIII (4.8 g, 6.8 mmol) in methanol (20 ml), 1 N sodium hydroxide (10.2 ml) was added at room temperature. After 2 h, water (10 ml) was added to the reaction mixture and the solution was concentrated to remove the organic solvent and washed with ether. The aqueous layer was cooled to 0~5° and acidified with citric acid to pH 4. The resulting oil was extracted with ethyl acetate and dried over sodium sulfate. The solution was evaporated and the residual oil was triturated with petroleum ether. The solid obtained was recrystallized from ethyl acetate-petroleum ether;

(i) Boc-Val-Pro-Gly-Lys(ε-Z)-Gly-ONp (X)

p-Nitrophenyl trifluoroacetate (1.21 g, 5.16 mmol) was added to a solution of IX (3.0 g, 4.3 mmol) in pyridine (20 ml) and the mixture was stirred for 24 h at room temperature. The reaction mixture was evaporated and the residue, dissolved in chloroform, was washed with 10% citric acid solution, 4% sodium bicarbonate solution, water and dried over sodium sulfate. The solution was evaporated and the residual oil was triturated with petroleum ether. The solid obtained was recrystallized from chloroform-petroleum ether; yield 2.74 g (78%), m.p. 113–118° C., $Rf^1$ 0.56, $Rf^3$ 0.92. Calcd. for $C_{39}H_{54}N_7O_{12}$: C, 57.62; H, 6.70; N, 12.06%. Found: C, 58.00; N, 6.74; N, 11.80%.

(j) H-Val-Pro-Gly-Lys(ε-Z)-Gly-ONp.TFA (XI)

A solution of X (1.3 g, 1.6 mmol) in 99% trifluoroacetic acid (2 ml) was allowed to stand for 10 min at room temperature. The reaction mixture was evaporated at low temperature and then dried in vacuo on potassium hydroxide in a desiccator at room temperature. The resulting solid was recrystallized from chloroform-ether; yield 1.1 g (83%), m.p. 130–135° C., $Rf^1$ 0.22, $Rf^3$ 0.79. Calcd. for $C_{36}H_{47}N_7O_{12}F_3$: C, 52.30; H, 5.73; N, 11.86%. Found: C, 52.50; H, 5.82; N, 11.63%. Amino acid analysis: Pro, 1.04; Gly, 2.08; Val, 0.89; Lys, 1.00.

(k) H-Val-Pro-Gly-Val-Gly-ONp.TFA (XII)

Boc-Val-Pro-Gly-Val-Gly-ONp (3.2 g, 4.93 mmol) prepared as described in Urry et al. (1975) J. Mol. Biol. 96, pp. 101–117, was dissolved in 99% trifluoroacetic acid (6 ml) and the mixture was treated in the same manner as described for the preparation of XI in part (j); yield 3.1 g (95%), m.p. 122–127° C., $Rf^1$ 0.13, $Rf^3$ 0.42. Calcd. for $C_{27}H_{37}N_6O_{10}F_3 \cdot \frac{1}{2}H_2O$: C, 48.29; H, 5.70; N, 12.51%. Found: C, 48.00; H, 5.86; N, 12.21%. Amino acid analysis: Pro, 1.00; Gly, 1.90; Val, 2.09.

(l) H-(Val-Pro-Gly-(ε-Z)-Gly)$_n$-Val-OMe (XIII)

To a solution of XI (0.77 g, 0.93 mmol) and XII (3.07 g, 4.6 mmol) in dimethyl sulfoxide (15 ml), triethylamine (1.16 ml, 8.30 mmol) and H-Val-OMe.HCl (2.3 mg, 0.014 mmol) were added. After stirring for 5 days at room temperature, triethylamine (0.016 ml, 0.111 mmol) and H-Val-OMe.HCl (18.6 mg, 0.111 mmol) were added to the solution and it was stirred for additional 2 days at room temperature. The reaction mixture was dialyzed against water at 0° and lyophilyzed; yield 2.1 g (86%), m.p. 295–298° C. (decomp.), $Rf^3$ 0.78. Amino acid analysis: Pro, 5.05; Gly, 10.08; Val, 9.02; Lys, 1.00. This polypentapeptide was composed of -Val-Pro-Gly-Val-Gly- sequence (ca. 80%) and -Val-Pro-Gly-Lys(ε-Z)-Gly- sequence (ca. 20%). Lysine content of polypentapeptide was ca. 4%.

(m) Boc-Val-Pro-Gly-OH (XIV)

III (28.6 g, 74.2 mmol) was saponified and treated in the same manner as described for the preparation of IX in part (j). The resulting oil was triturated with ether and petroleum ether. A hygroscopic solid was obtained; yield 20.3 g (74%), m.p. 63–67° C., $Rf^1$ 0.37. Calcd. for $C_{17}H_{29}N_3O_6 \cdot \frac{1}{2}H_2O$: C, 54.09; H, 7.92; N, 11.13%. Found: C, 53.52; H, 7.67; N, 11.14%.

(n) Boc-Val-Pro-Gly-ONp (XV)

To a solution of XIV (4.4 g, 11.8 mmol) in pyridine (30 ml) was added p-nitrophenyl trifluoroacetate (3.22 g, 13.7 mmol). After stirring for 24 h at room temperature, the reaction mixture was treated in the same manner as described for the preparation of X. An oil obtained gave a single spot on TLC; yield 5.67 g (98%), $Rf^1$ 0.60.

(o) Z-Gly(γ-OBu$^t$)-Gly-OMe (XVI)

Z-Glu(γ-OBu$^t$)-OH (6.07 g, 18.0 mmol) and H-Gly-OMe.HCl (2.71 g, 21.6 mmol) were reacted by the mixed anhydride method as described for the preparation of I in part (a). The resulting oil showed a single spot on TLC; yield 6.8 g (93%), $Rf^1$ 0.62.

(p) H-Glu(γ-OBu$^t$)-Gly-OMe.HCl (XVII)

A solution of XVI (6.8 g, 16.6 mmol) and pyridine.HCl (1.92 g, 16.6 mmol) in methanol (30 ml) was hydrogenated in the presence of palladium-charcoal catalyst for 12 h at room temperature. The catalyst was removed by filtration and the filtrate was evaporated. Ether was added to the residue and the precipitate ($Rf^2$ 0.23) developed was removed by filtration and the filtrate was evaporated to dryness. An oil obtained gave a single spot on TLC; yield 2.89 g (56%), $Rf^1$ 0.26, $Rf^2$ 0.72. The precipitate ($Rf^1$ 0.23) was presumed to be a cyclic dipeptide from the data of elemental analysis.

(q) Boc-Val-Pro-Gly-Glu(γ-OBu$^t$)-Gly-OMe (XVIII)

To a solution of XV (1.66 g, 3.38 mmol) in dimethyl formamide (5 ml) were added XVII (1.05 g, 3.38 mmol) and triethylamine (0.57 ml, 4.06 mmol) in dimethyl formamide (5 ml) and the mixture was stirred for 2 days at room temperature. The reaction mixture was evaporated and the residue, dissolved in ethyl acetate, was washed with 10% citric acid solution, 4% sodium bicarbonate solution, water and dried over sodium sulfate. The solution was evaporated to dryness. An oil obtained gave a single spot on TLC; yield 1.64 g (77%), $Rf^1$ 0.57.

(r) Boc-Val-Pro-Gly-Glu(γ-OBu$^t$)-Gly-OH (XIX)

1 N sodium hydroxide (3.92 mol) was added to a solution of XVIII (1.64 g, 2.61 mmol) in methanol (15 ml) and the mixture was allowed to stand for 2 h at room temperature. The reaction mixture was treated in the same manner as described for the preparation of IX. The resulting oil showed a single spot on TLC; yield 1.32 g (82%), $Rf^1$ 0.14.

(s) Boc-Val-Pro-Gly-Glu(γ-OBu$^t$)-Gly-ONp (XX)

XIX (1.32 g, 2.15 mmol) and p-nitrophenyl trifluoroacetate (0.607 g, 2.58 mmol) were reacted in pyridine (10 ml) in the same manner as described for the preparation of X in part (b). The resulting oil was triturated with ether and petroleum ether. The solid obtained was composed of one major component ($Rf^1$ 0.44) and one minor component ($Rf^1$ 0.33). Repeated recrystallization from chloroform-petroleum ether and further purifications using several organic solvents were attempted, but these attempts were only of limited effect in fractionating the major component as pure XX. The component (1.13 g, $Rf^1$ 0.44) containing only traces of the component ($Rf^1$ 0.33) was used in the next step without further purification.

(t) H-Val-Pro-Gly-Glu-Gly-ONp.TFA (XXI)

A solution of XX (1.1 g, 1.50 mmol) in 9 ml of 30% trifluoroacetic acid in methylene chloride was allowed to stand for 30 min. at room temperature. The reaction mixture was treated in the same manner as described for the preparation of XI in part (j). The resulting solid was recrystallized from chloroform-petroleum ether; yield 0.923 g (90%), m.p. 130–133° C., $Rf^1$ 0.06, $Rf^2$ 0.12, $Rf^3$ 0.21. Calcd. for $C_{27}H_{35}N_6O_{12}F_3 \cdot \frac{1}{2}H_2O$: C, 46.22; H, 5.17; N, 11.98%. Found: C, 46.06; H, 5.16; N, 11.82%. Amino acid analysis: Glu, 0.98; Pro, 0.90; Gly, 2.10; Val, 1.00.

(u) H-(Val-Pro-Gly-$\phi$-Gly)$_n$-Val-OMe (XXII)

To a solution of XXI (0.869 g, 1.25 mmol) and XII (3.31 g, 4.99 mmol) in dimethyl sulfoxide were added H-Val-OMe.HCl (2.7 mg, 0.016 mmol) and triethylamine (1.31 ml, 9.36 mmol). After stirring for 5 days at room temperature, the reaction mixture was treated in the same manner as described for the preparation of XIII in part (l); yield 1.9 g (72%), m.p. 285–290° C. (decomp.), $Rf^3$ 0.57. Amino acid analysis: Glu, 1.00; Pro, 5.08; Gly, 10.17; Val, 9.14. This polypentapeptide contained the -Val-Pro-Gly-Val-Gly- sequence (ca. 80%) and the -Val-Pro-Gly-Glu-Gly- sequence (ca. 20%). Glutamic acid content of polypentapeptide was about 4%.

(v) H-(Val-Pro-Gly-$\phi$-Gly)$_n$-Val-OMe (XXIII)

Anhydrous hydrogen bromide was bubbled into a chilled solution of XIII (270 mg) in absolute methanol (20 ml) for 10 min and then nitrogen was bubbled into the solution to remove excess hydrogen bromide. The reaction mixture was evaporated and dried in vacuo on potassium hydroxide in a desiccator. The residue, after neutralization with triethylamine, was dissolved in pyridine (10 ml) and dialyzed against water at 0° and lyophilized; yield 171 mg (ca. 69%), m.p. 295–300° C. (decomp.), $Rf^3$ 0.53. Amino acid analysis: Pro, 7.02; Gly, 13.96; Val, 13.00; Lys, 1.00. This polypentapeptide contained the -Val-Pro-Gly-Val-Gly- sequence (ca. 86%) and the -Val-Pro-Gly-Lys-Gly- sequence (ca. 14%). Lysine content of polypentapeptide was about 2.9%.

(w) Cross-Linked H-(Val-Pro-Gly-$\psi$-Gly)$_m$-Val-OMe (XXIV)

XXII (100 mg) and XXIII (140 mg) were dissolved in a small amount of water (0.7 ml) at 0–5° and the solution was placed in a 45 ml Virtis freeze-drying glass vessel mounted horizontally to a rotary drive. The solution, at a steady orientation, flowed on the inside of the vessel for 3 h at 40° as the vessel was rotated slowly. The flowing solution resulted in the formation of a thick coacervate which flowed to coat the internal surface of vessel. To this coating was added 3 g of ground 1-cyclohexyl-3-(2-morpholinoethyl)-carbodiimide metho-p-toluenesulfonate and the mixture flowed for 15 h at the same temperature. On addition of water (0.2 ml), the mixture was gradually cooled to 25° and allowed to flow for another 2 days. 10 ml of water was added to the reaction mixture and the turbid supernatant was decanted. This decantation was repeated several times and an insoluble product was seen to remain in the vessel. Amino acid analysis: Glu, 2.05; Pro, 21.95; Gly, 43.02; Val, 39.86; Lys, 1.00.

Prior to cross-linking with the flow orientation described above, XXII and XXIII were cross-linked in a test tube by means of the same coupling reagent as above without flow orientation after the formation of coacervates at 38–40°. The cross-linked polypentapeptide obtained without flow orientation was insoluble not only in aqueous solutions but also in organic solvents as was the product obtained with flow orientation.

The cross-linked polypentapeptide prepared according to the above example is inherently fibrillar and anisotropic in nature and exhibits elastomeric properties which are dependent on the water content of the matrix. At high water contents the elastic modulus is less than that of wet native aortic elastin and becomes greater on drying.

Proton magnetic resonance studies using DMSO as solvent were carried out on a Varian HR-220 MHz spectrometer equipped with a tracking frequency decoupling accessory and an SS-100 computer system with 16K of core for multiscan averaging. Sample temperature was calibrated wth methanol or ethylene glycol chemical shifts and controlled to within ±2° C.

Figure 1B:
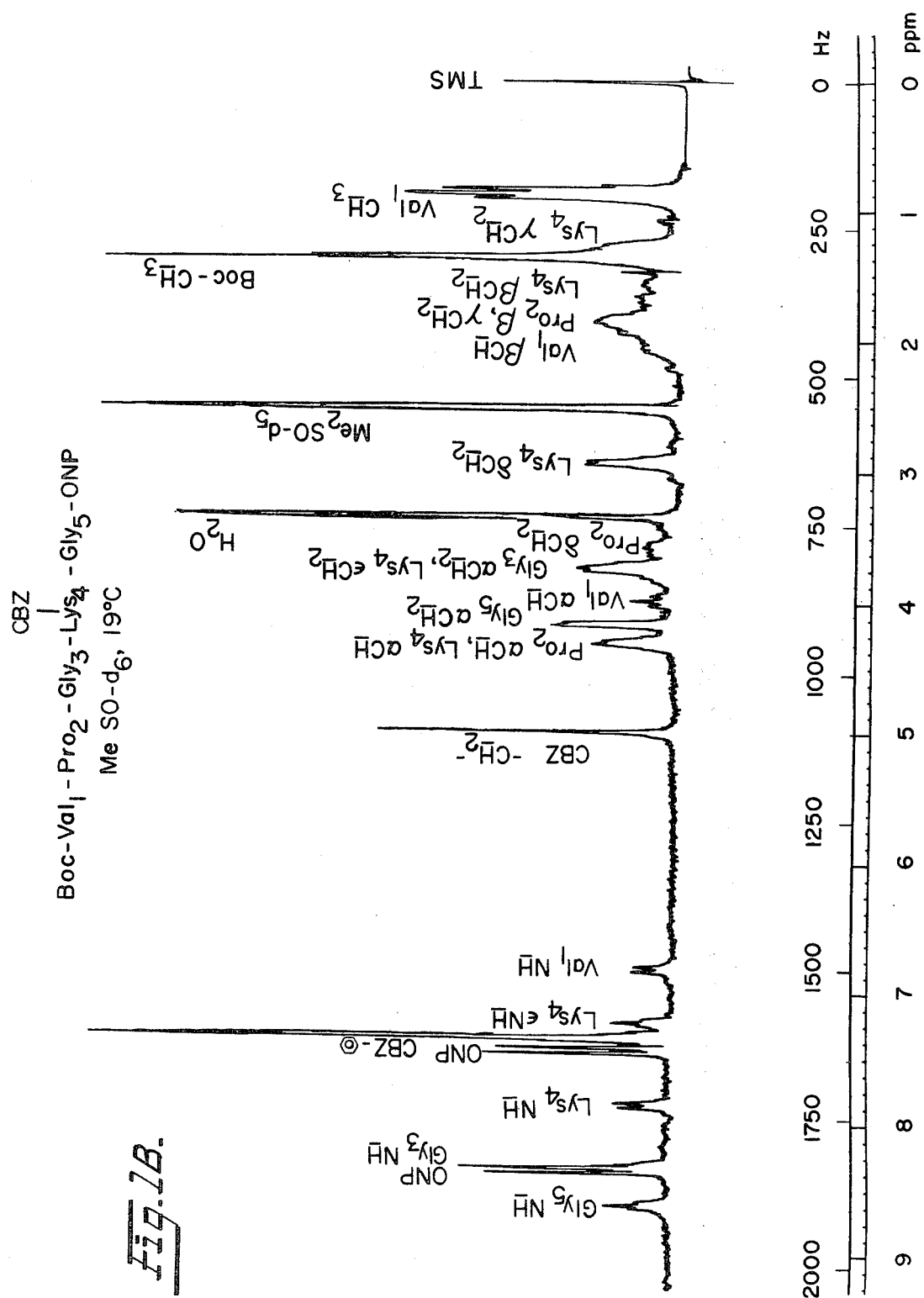
Figure 1C:
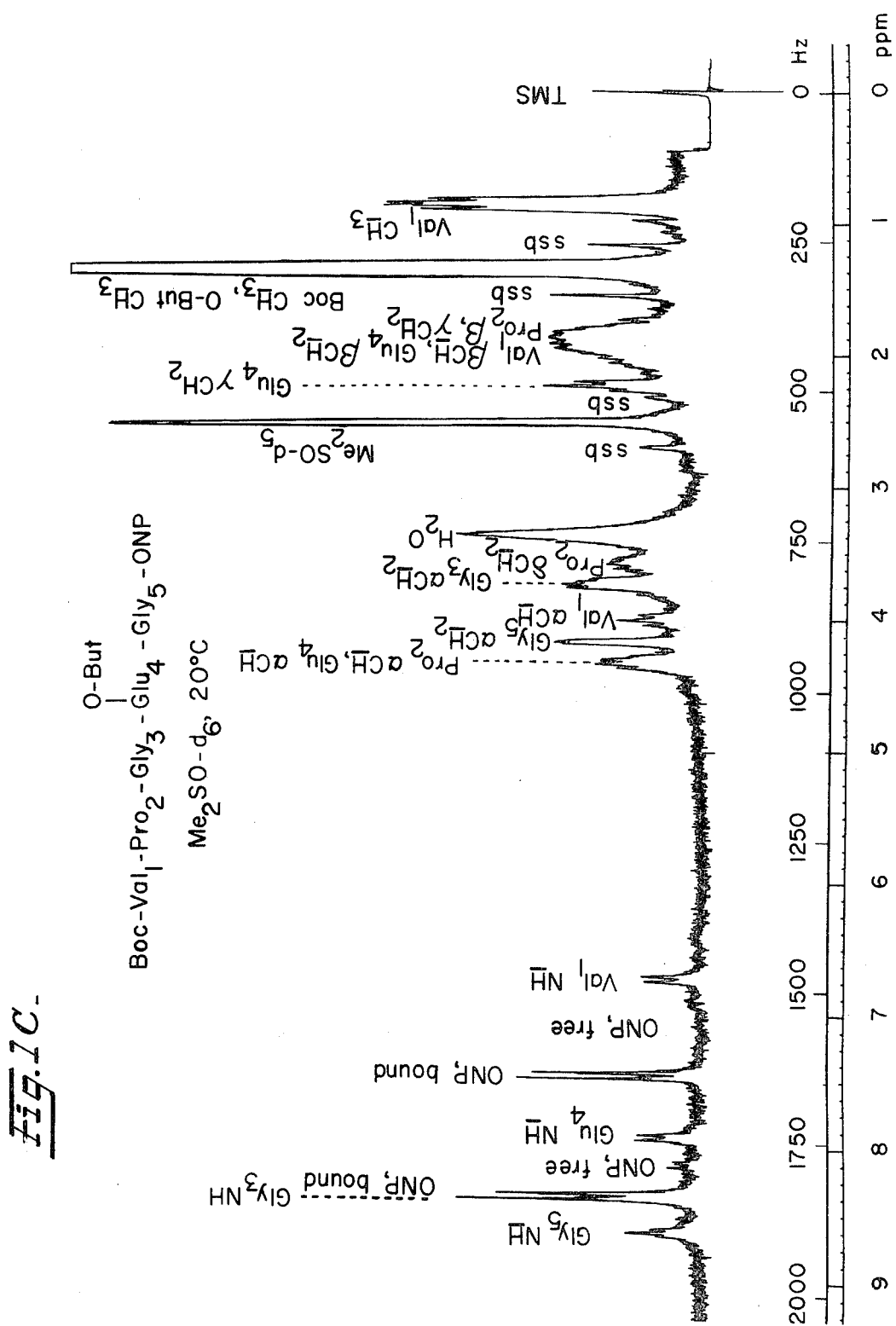

As will be apparent, the three pentameric units which are incorporated into the cross-linked high polymers are $Val_1$-$Pro_2$-$Gly_3$-$Val_4$-$Gly_5$, $Val_1$-$Pro_2$-$Gly_3$-$Lys_4$-$Gly_5$, and $Val_1$-$Pro_2$-$Gly_3$-$Glu_4$-$Gly_5$. Proton magnetic resonance spectra at 220 MHz of all three as the Boc and Np derivatives, of the second with the $\epsilon$-amino group blocked by benzyloxycarbonyl, and of the third with the $\gamma$-carboxyl blocked by a t-butyl ester are given in FIGS. 1A, 1B and 1C of the drawings. In the peptide NH region the highest field doublet near 1500 Hz is the $Val_1$ NH; the lowest field triplet is due to the $Gly_5$ NH, and the pair of intense doublets are due to the p-nitrophenyl moiety in all three spectra. In the spectrum of the first of the pentameric units, the remaining doublet is due to the $Val_4$ NH and the resonance just to the high field side of the lowest field p-nitrophenyl doublet is due to the $Gly_3$ NH. In the spectrum of the second of the units, the most intense resonance is due to the aromatic protons of the benzyloxycarbonyl moiety and the $\epsilon$-NH triplet is immediately on its high field side. The $Lys_4$ NH is between the two-p-nitrophenyl resonances. Otherwise the resonances are as in the first spectrum with the slight shifts which cause the low field p-nitrophenyl doublet to overlap the $Gly_3$ NH resonance. In the spectrum of the third of the units, the $Glu_4$ NH is central between the intense aromatic doublets, and the low field aromatic doublet and the $Gly_3$ NH resonance overlap. The remainder of the resonances in the peptide NH region of the third spectrum are as in the first. One can similarly look at the higher field regions and verify that the syntheses are correct and that there are no dramatic differences that would argue for differences in conformation.

Figure 2A:
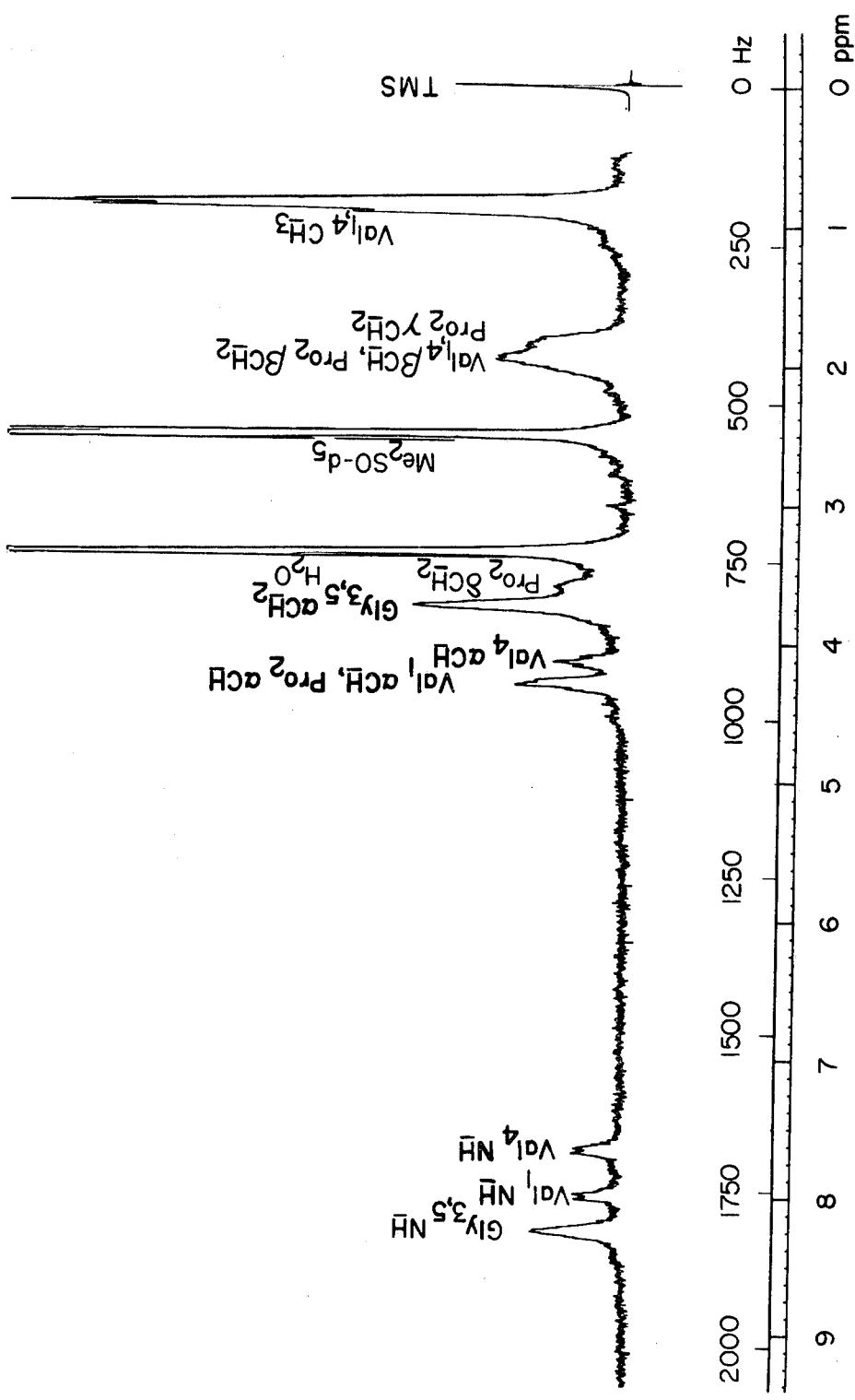
Figure 2B:
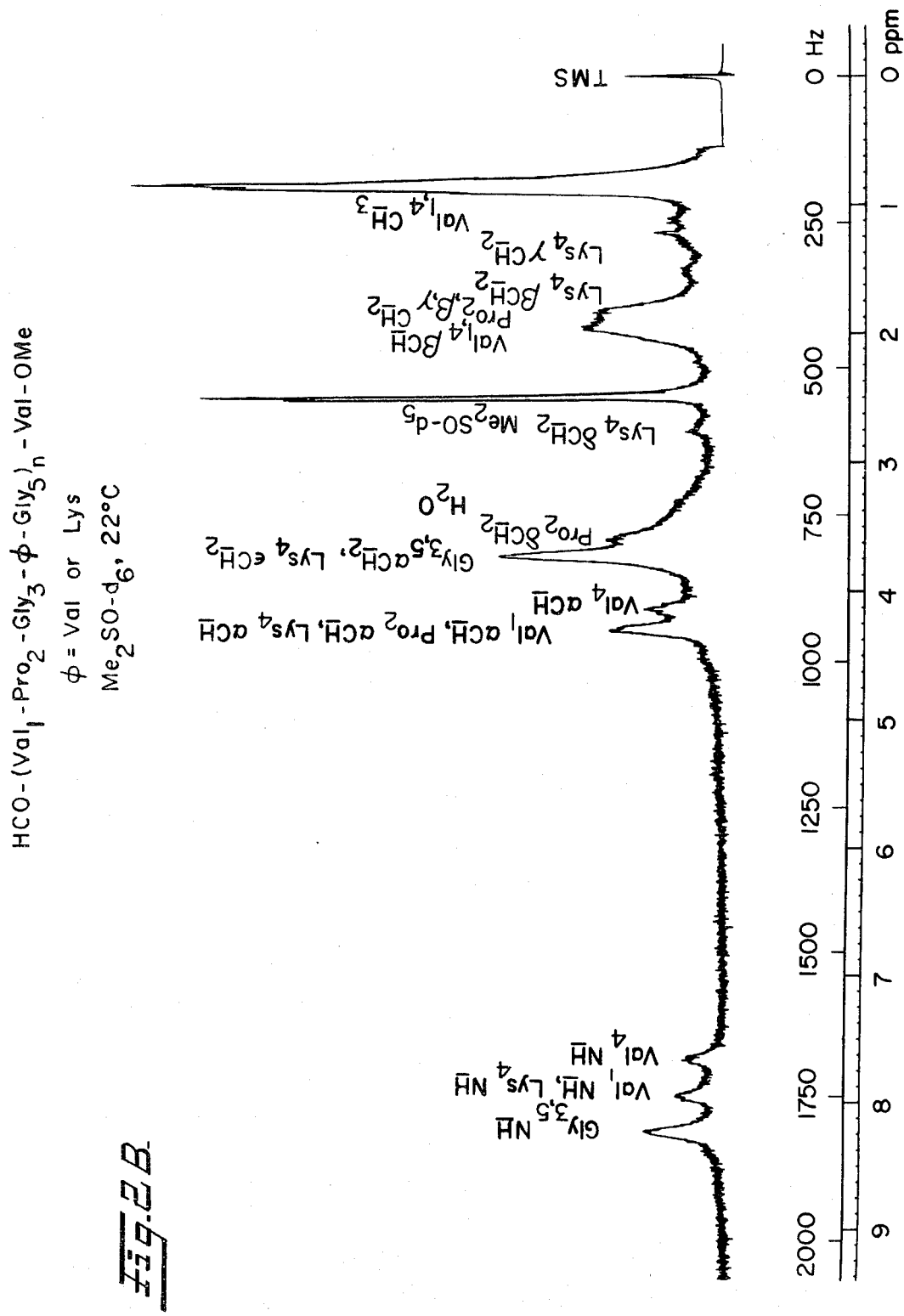
Figure 2C:
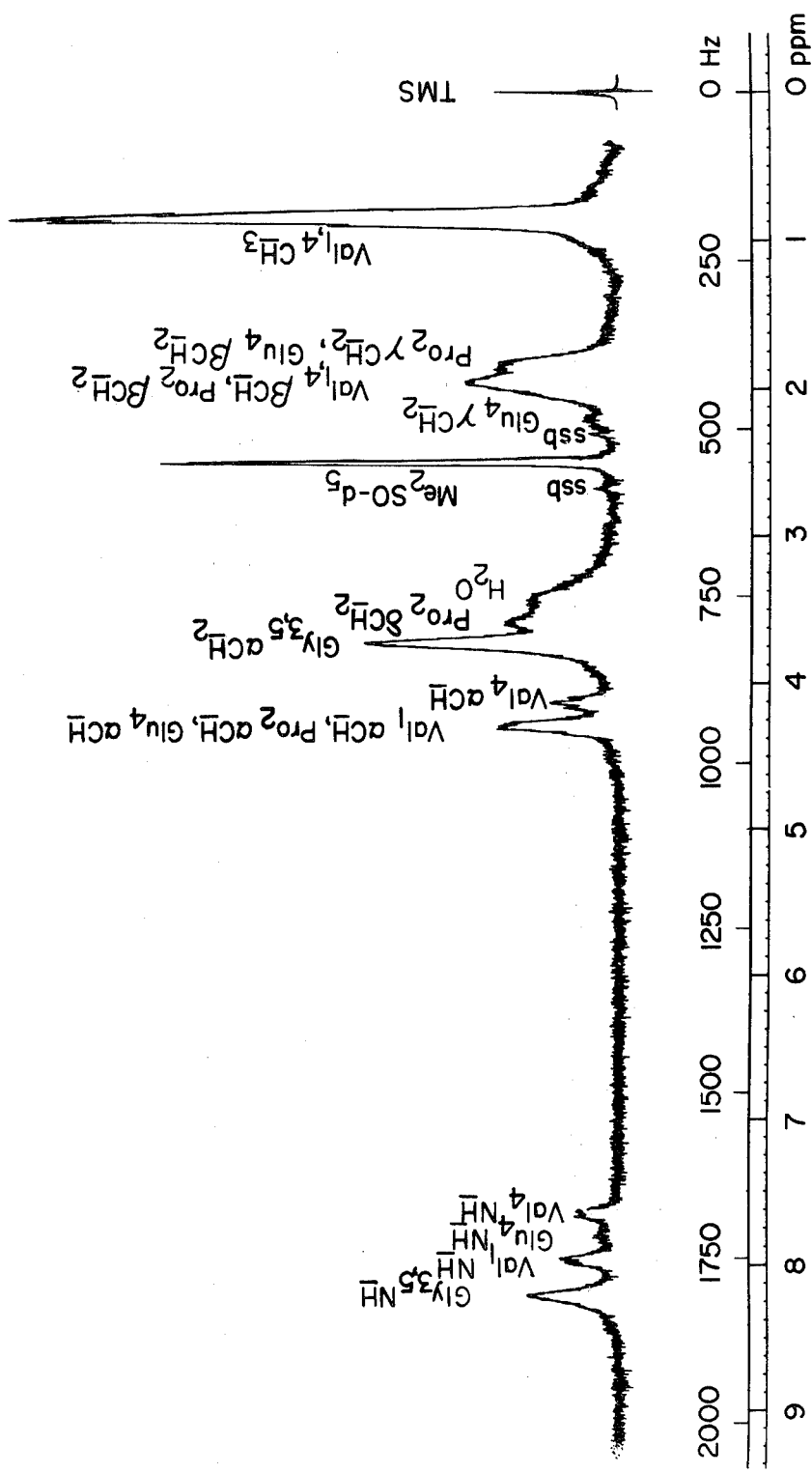

In FIGS. 2A, 2B and 2C of the drawings, there are shown in descending order for the purpose of comparison, the proton magnetic resonance spectra of the high polymer, without the Glu and Lys cross-linking residues and those of the high polymers XXIII and XXII. The spectra when carefully analyzed, with scale expansion and multiscanning, are entirely consistent with the amino acid analyses of XXII and XXIII. These high polymers coacervate as does the polypentapeptide such that cross-linking can be carried out in the coacervate state, and it is believed that the properties of the cross-linked polypentapeptide are those of the polypentapeptide aside from the solubility factor.

Scanning electron-microscopy studies were carried out by placing the insoluble cross-linked polypentapeptide formed without flow orientation and with flow orientation on a glass and Plexiglas substrate, respectively, dried in a vacuum oven, and coated with several hundred Angstroms of Au-Pd evaporated at less than 5 × 10$^{-5}$ mm Hg. The cross-linked polypentapeptides were then examined in a JEOL JSM-U3 scanning electron microscope at a 25 kV accelerating voltage.

Figure 3:
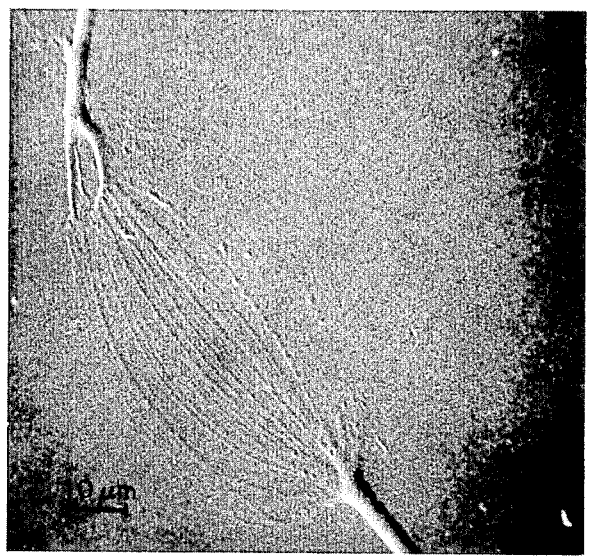
FIG. 3 is a scanning electron micrograph of an area of a preferred cross-linked high polymer of the invention wherein cross-linking was effected under static conditions.

Solutions of the polymers XIII and XXII, which were cross-linked in a test tube without flow, exhibited fibers. One such fiber is seen in FIG. 3. The fiber in this scanning electron micrograph is seen to splay out at a bend showing the presence of many component fibrils and to recoalesce into a single fiber again. Whereas an isotropic coalescence would simply show spheres, this two-dimensional coalescence clearly demonstrates the fundamental anisotropic nature of the fibers formed from the cross-linked polypentapeptide according to the invention, and it reflects the filamentous substructure.

Figure 4:
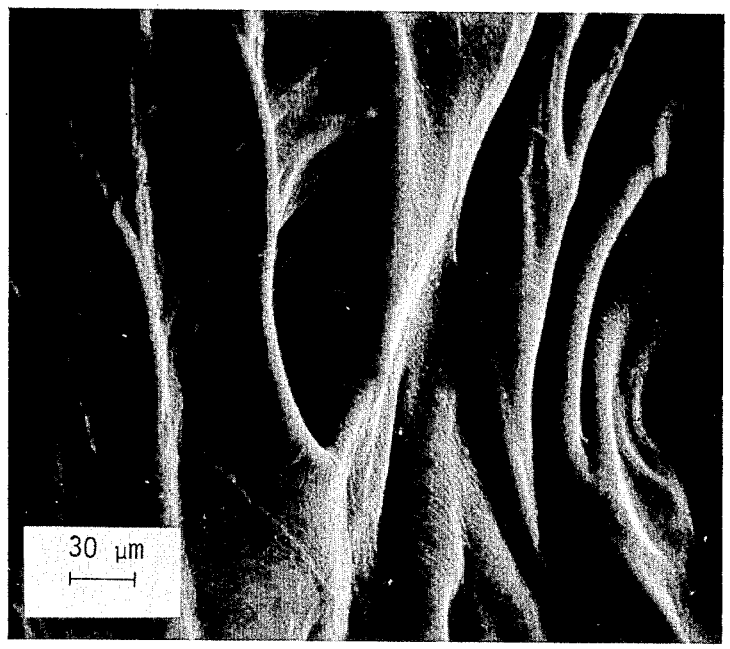
FIG. 4 is a scanning electron micrograph of an area of a preferred cross-linked high polymer of the invention wherein cross-linking was effected by a flow orientation technique.

The cross-linked polymer formed by flow orientation is the thick matted matrix seen in the scanning electron micrograph of FIG. 4. On taking the band forming the coating on the flask, after washing and folding it, enough material can be obtained to test its elastomeric nature. The material is very sticky, adhering to almost any surface, and when pulled from its attachment with a pair of tweezers it snaps back like a rubber band. This elastomeric behavior is dependent on the amount of water present as it decreases with increasing water content as will be shown below.

Figure 5:
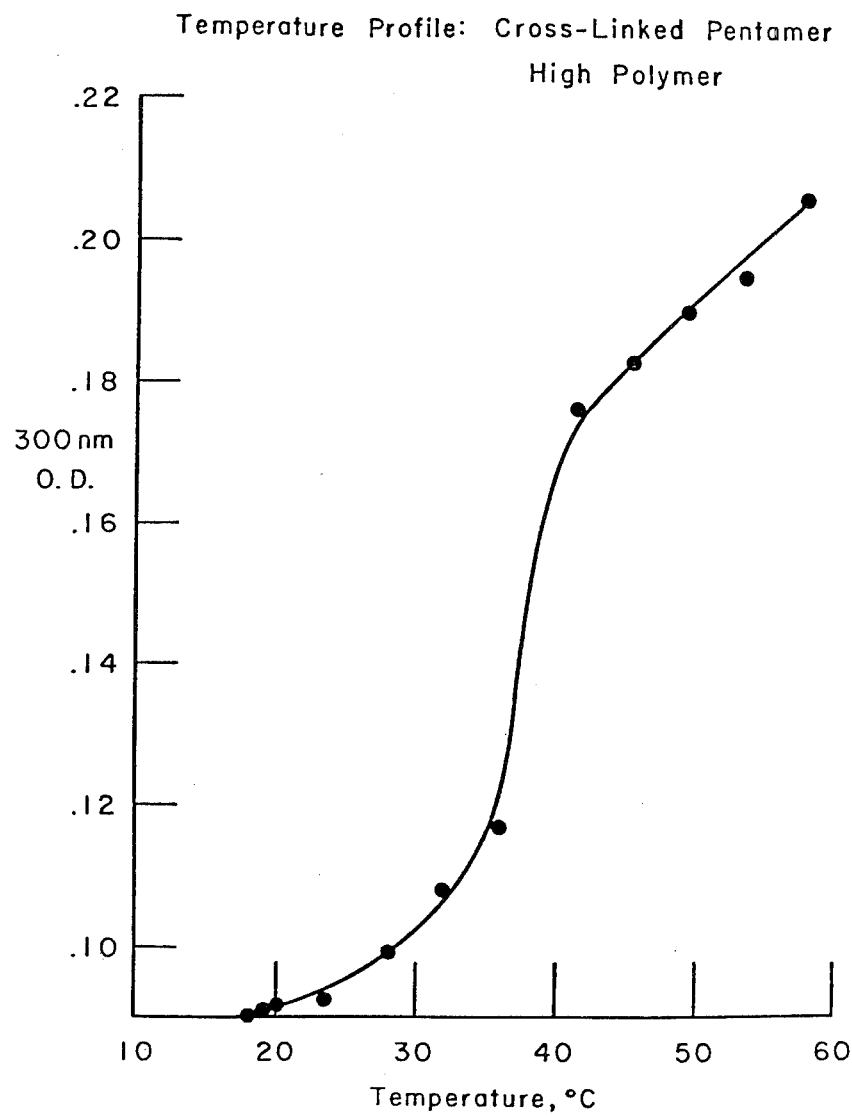
FIG. 5 is a graph showing the reversible temperatureelicited swelling and retraction characteristics of a preferred cross-linked high polymer of the invention.

The weakly cross-linked polypentapeptide product XXIV, undergoes a reversible temperature-elicited swelling and retraction, the latter of which is directly analogous to coacervation. The temperature profile for this purpose, as shown by the graph of FIG. 5, is very similar to the temperature profile for coacervation of concentrated solutions of polypentapeptide as described in Urry et al. (1974) Biochemistry, 13, 609 and Urry et al. (1975) Int. Res. Commun. Syst. 3, 572. The retracted state is simply the cross-linked coacervate state and the swollen gel-like state would be a solution if it were not for the cross-links.

Stress-strain studies were carried out using a system consisting of a moving platform supported by linear motion ball bearings riding on a steel shaft. This moving assembly is driven by a lead screw coupled to an induction motor through a variable speed gear drive. A clamp on the platform holds one end of the specimen. Platform position is recorded on the x axis of an x-y recorder using a linear displacement transducer, bridge completion network and a d-c excitation power supply. The fixed end of the specimen is held by a clamp attached to a load cell. The load cell consists of a Statham Universal Transducing Cell (UC3) with a UL4-0.5 load cell accessory. Signal conditioning is done by a d-c excitation power supply, balance network and a signal amplifier. The output signal is an analog voltage of the applied force which is recorded on the y axis of the x-y recorder.

A force-strain curve was recorded by placing one end of the specimen in the load cell clamp which was detached from the load cell. The other end of the specimen was clamped to the platform. The load-cell clamp was then attached to the load cell with an initial length of 1 mm and no initial tensile or compressive force. The drive was turned on and the specimen stretched at a rate of one-half millimeter per second.

Figure 6:
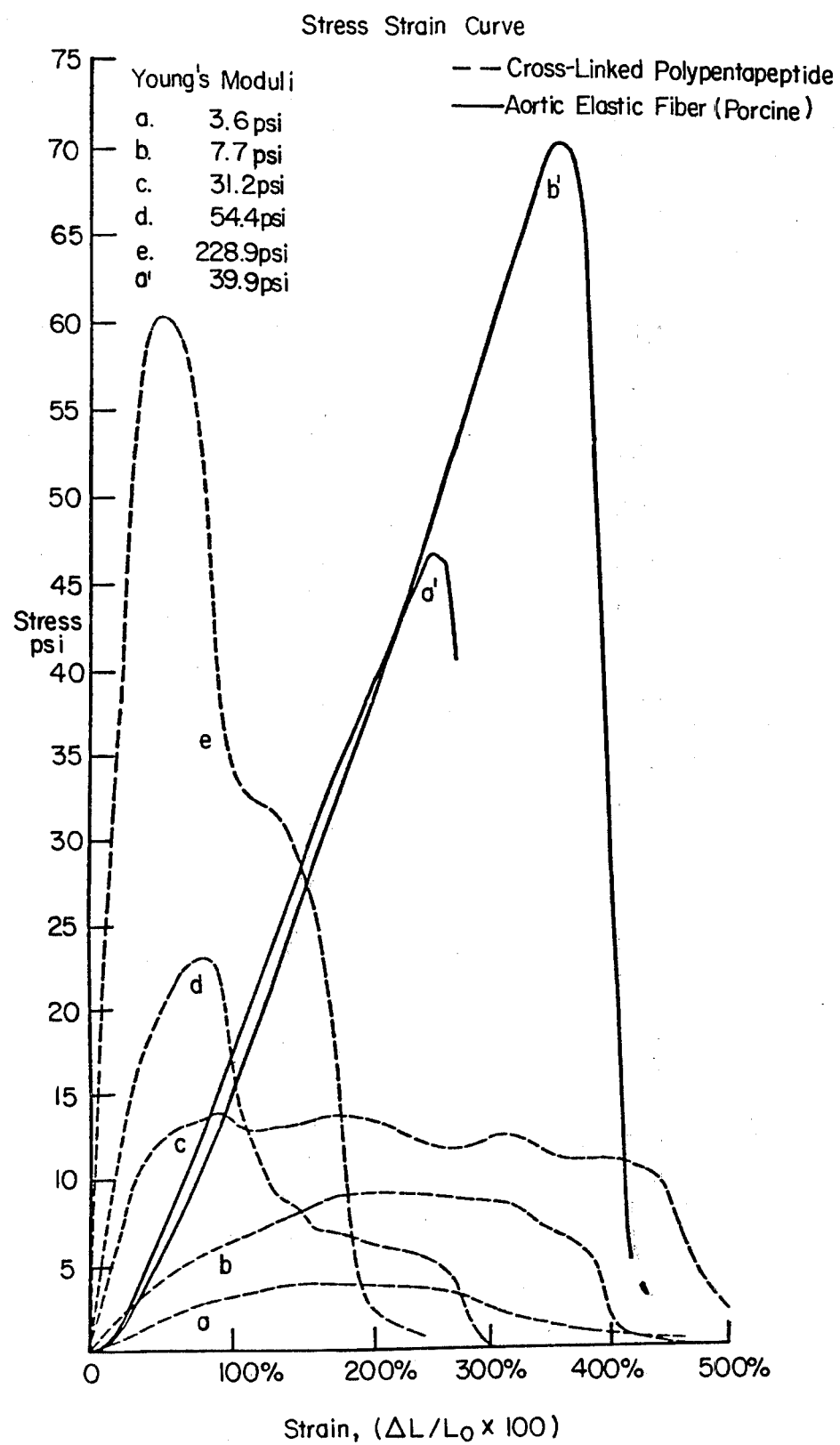
FIG. 6 is a depiction in graph form of a comparison between the elastomeric properties of a preferred cross-linked high polymer of the invention and those of native aortic elastin.

The elastomeric properties of the cross-linked polypentapeptide are demonstrated in the graphs of FIG. 6 and compared to those of native aortic elastin. At room temperature the water content of the cross-linked polypentapeptide of the invention can be varied by addition of a given quantity and then by allowing the specimen to dry with time. When the polymer contains 70% water by weight it exhibits very little elasticity, curve a of FIG. 6. On drying with the time the initial slopes of the stress-strain curves increase dramatically to become greater than those of wetted native aortic elastin, curves a' and b' of FIG. 6. The elastic modulus of the cross-linked polymer increases from 3.6 psi at 70% water to 230 psi where the sample is becoming so dry that it becomes brittle. The undulations in the curves for the cross-linked polypentapeptide of the invention are due to breaking of a composite strand and resultant flow. The abrupt drops in the curves at higher strain are due to complete rupture of the sample. The curves in FIG. 6 demonstrate that the elastomeric properties are solvent dependent and comparison with FIG. 5 allows the correlation to be made between the elastomeric state and the coacervate state.

The insoluble cross-linked polypeptide of the example, especially when formed by the flow orientation technique, has been found to be particularly suitable as a serum calcifiable matrix, making it adaptable for use in the formation and repair of bone structure in the animal. It will calcify from serum alone even when separated from the serum medium by a dialysis membrane with a low molecular weight cut off. By microprobe analysis, it appears that the only serum elements required for the calcification are calcium and phosphorus. Furthermore, thin sections of the calcified matrix showed the calcification to occur throughout the matrix and thereby verifies that it is a bulk property of the matrix and not an interfacial property. It is believed that this is the first demonstration of an insoluble, synthetic polypeptide to function in this manner.

The calcification of the cross-linked polypentapeptide was followed in three different systems: (1) in serum with added $CaCl_2$ and $KH_2PO_4$, (2) in serum alone and (3) in serum, with dialysis tubing separating the polypentapeptide from the serum. For systems one and two, the synthetic peptide was applied with a spatula to a small Plexiglas block (Rohm and Haas, Philadelphia, Pa.) and allowed to dry with heating at 40° C. The polypeptide adhered to this support throughout all of the incubation time for each experiment. In the case of system three, the cross-linked material was applied directly to the inside of one-fourth inch width dialysis tubing with a 12,000 m.w. cut off (Arthur H. Thomas Co., Philadelphia, Pa.).

In the first set of experiments 1 ml of sterile bovine serum (Microbiological Associates, Bethesda, Md.) which had previously been incubated at 37° C. for 24 hours, was made 1.5 mM in one experiment and 3mM in another experiment with respect to added $CaCl_2$ and $KH_2PO_4$ (Starcher, et al., 1974). Both salts were added as sterilized aqueous solutions. This serum was added to the polypentapeptide which had been autoclaved for 20 min. at 115° C. for the 1.5 mM ion addition but not for the 3mM addition. The samples were incubated with shaking at 37° C. for 3½ days for the 1.5 mM experiment and 2 days for the 3 mM experiment. After incubation, the serum was pipetted off and each sample was rinsed two times with 2 ml of 37° C. glass distilled water and 2 ml of 37° C. absolute ethanol. The samples were then dried with heat under vacuum for 60 minutes and examined with SEM and microprobe analysis. Calcification occurred in all experiments regardless of autoclaving.

In the second set of experiments, the polypentapeptide was incubated at 37° C. with serum alone; in one experiment for 15 days with a total of 7 ml of sterile bovine serum, in another for 7 days with a total of 35 ml of serum, and in another for 14 days with 70 ml of serum. For the last two experiments, the serum was changed daily in 5 ml aliquots. Calcification proceeded in both autoclaved and non-autoclaved polypentapeptide samples.

In the third set of experiments, the synthetic peptide was placed inside dialysis tubing, autoclaved, the incubated at 37° C. against 15 ml of sterile bovine serum changed daily for 7 days. The total volume of serum was 105 ml. As in the first two sets of experiments, controls without polypeptide were also run.

Following calcification, the specimens were examined at 30X with a light microscope, dried in a vacuum oven at 60° C., and then coated with several hundred Angstroms of evaporated aluminum at less than $5 \times 10^{-5}$ mm Hg. Examination in a JEOL JSM-U3 Scanning Electron Microscope was used to assess the extent of calcification, by means of an EDAX Model 707A solid state x-ray detector and analyzer, and to view the surface features of the calcified material. After completing these preliminary checks, the sample was removed from the support used during calcification by lifting small portions loose with a metal probe. These portions were placed in "Beem" capsules, oriented to yield the desired cross-section upon sectioning, and embedded with Araldite 502 supplied by Ladd Research Laboratories, Inc. The epoxy was cured at 50-60° C. overnight in a vacuum oven. After curing, the samples were sectioned to the desired thickness (usually 0.5 to 1 micron) with an LKB 8800 Ultratome using glass knives. The sections were floated on distilled water which was maintained above 40° C., and collected on 180 mesh carbon coated nylon grids supplied by E. F. Fullam, Inc. These were immediately air dried (by a heat lamp), mounted on 1" diameter carbon stubs, and coated with several hundred Angstroms of aluminum as described previously. Scanning electron microscopy and x-ray microanalysis of the sections were performed at 25 kV. Elemental mapping and x-ray line profiles were used to determine the distribution of calcification throughout the entire sample cross-section, and to define the occurrence and distribution of other elements heavier than fluorine in the samples.

In all instances, it was demonstrated that, as indicated above, calcification occurs throughout the matrix.

It will be obvious from this that the cross-linked synthetic polypentapeptide of the example prepared by flow orientation would not of itself, because of its highly serumcalcifiable nature, be suitable for use as artificial vascular wall material. However, when inactivated, as described above, the cross-linked polymer, shaped, as is also described above, is admirably suited for this purpose.

Having described our invention, we claim:

1. A process for preparing a synthetic elastomeric water-insoluble polypentapeptide, comprising cross-linking a first linear polypentapeptide and a second linear polypentapeptide, said first linear polypentapeptide being one consisting essentially of first pentapeptide units ($Val_1Pro_2Gly_3Val_4Gly_5$) and second pentapeptide units in which one of the amino acid residues of said first pentapeptide unit is replaced by the residue of an amino acid having more than one amino function and said second linear polypentapeptide being one consisting essentially of first pentapeptide units ($Val_1Pro_2Gly_3Val_4Gly_5$) and second pentapeptide units in which one of the amino acid residues of said first pentapeptide unit is replaced by the residue of an amino acid having more than one carboxyl function, said cross-linking being effected by the presence of an effective amount of an agent which causes reaction between free amino functions of said first linear polypentapeptide and free carboxyl functions of said second linear polypentapeptide.

2. A process as claimed in Claim 1 in which said residue of an amino acid having more than one amino function is the residue of lysine and said residue of an amino acid having more than one carboxyl function is the residue of glutamic acid.

3. A process as claimed in claim 2 in which said residue of lysine and said glutamic acid residue both replace the $Val_4$ residue of said pentapeptide unit ($Val_1Pro_2Gly_3Val_4Gly_5$).

4. A process as claimed in claim 3 in which the ratio of $Val_4$ to Lys in said first linear polypentapeptide is within the range of 1:1 to 10:1 and the ratio of $Val_4$ to Glu in said second linear polypentapeptide is within the range of 1:1 to 10:1.

5. A process as claimed in claim 4 in which the ratio of $Val_4$ to Lys in said first linear polypentapeptide is about 3:1 and the ratio of $Val_4$ to Glu in said second linear polypentapeptide is about 3:1.

6. A process as claimed in claim 4 in which the number of pentapeptide units in each of said linear polypentapeptides is within the range of about 10 to 100.

7. A process as claimed in claim 6 in which the number of pentapeptide units in each of said linear polypentapeptides is about 40.

8. A process as claimed in claim 4 in which the ratio of said first linear polypentapeptide to said second linear polypentapeptide is within the range of 4:1 to 1:4.

9. A process as claimed in claim 8 in which the $Val_4$:Lys and $Val_4$:Glu ratios are the same and the ratio of said first linear polypentapeptide to said second linear polypentapeptide is about 1:1.

10. A product consisting essentially of the synthetic elastomeric insoluble polypentapeptide prepared by the process claimed in claim 1.

11. A product consisting essentially of the synthetic elastomeric insoluble polypentapeptide prepared by the process claimed in claim 2.

12. A product consisting essentially of the synthetic elastomeric insoluble polypentapeptide prepared by the process claimed in claim 3.

13. A product consisting essentially of the synthetic elastomeric insoluble polypentapeptide prepared by the process claimed in claim 4.

14. A product consisting essentially of the synthetic elastomeric insoluble polypentapeptide prepared by the process claimed in claim 5.

15. A product consisting essentially of the synthetic elastomeric insoluble polypentapeptide prepared by the process claimed in claim 6.

16. A product consisting essentially of the synthetic elastomeric insoluble polypentapeptide prepared by the process claimed in claim 7.

17. A product consisting essentially of the synthetic elastomeric insoluble polypentapeptide prepared by the process claimed in claim 8.

18. A product consisting essentially of the synthetic elastomeric insoluble polypentapeptide prepared by the process claimed in claim 9.

* * * * *